United States Patent [19]

DeLuca et al.

[11] Patent Number: 4,555,364

[45] Date of Patent: Nov. 26, 1985

[54] METHOD FOR PREPARING 1-HYDROXYVITAMIN D COMPOUNDS

[75] Inventors: Hector F. DeLuca; Heinrich K. Schnoes; Seok H. Lee, all of Madison; Mary E. Phelps, Stoughton, all of Wis.

[73] Assignee: Wisconsin Alumni Research Foundation, Madison, Wis.

[21] Appl. No.: 667,296

[22] Filed: Nov. 1, 1984

[51] Int. Cl.$^4$ .............................................. C07J 9/00
[52] U.S. Cl. .................................................. 260/397.2
[58] Field of Search ..................................... 260/397.2

[56] References Cited

U.S. PATENT DOCUMENTS 4,367,177 1/1983 DeLuca et al. ................. 260/397.2
4,512,925 4/1983 DeLuca et al. ................. 260/397.2

Primary Examiner—Elbert L. Roberts
Attorney, Agent, or Firm—Howard W. Bremer

[57] ABSTRACT

The invention relates to a process for preparing 1-hydroxyvitamin D compounds by acid-catalyzed solvolysis of the corresponding 1-hydroxy-3,5-cyclovitamin D compound in an organic solvent medium whereby the free, non-acylated, 5,6-cis and 5,6-trans-1-hydroxylated vitamin D compounds are obtained in admixture.

11 Claims, No Drawings

METHOD FOR PREPARING 1-HYDROXYVITAMIN D COMPOUNDS

DESCRIPTION

This invention was made with Government support under NIH Grant No. AM-14881 awarded by the Department of Health and Human Services. The Government has certain rights to this invention.

TECHNICAL FIELD

This invention relates to hydroxylated vitamin D compounds. More specifically, the invention relates to a method for preparing 1-hydroxyvitamin D compounds from 3,5-cyclovitamin D intermediates.

BACKGROUND ART

It is known that the physiological actions of vitamin D, namely the maintenance of calcium and phosphate homeostasis and the proper mineralization of bone, is dependent on the in vivo metabolism of the vitamin to hydroxlyated derivatives. Particularly important are 1-hydroxylated vitamin D metabolites, and one of these, 1α,25-dihydroxyvitamin $D_3$, is indeed generally regarded as the physiologically active hormonal form of vitamin $D_3$. This compound and certain of its 1-hydroxylated structural analogues, e.g. 1α-hydroxyvitamin $D_3$, 1α-hydroxyvitamin $D_2$ and 1α,25-dihydroxyvitamin $D_2$, and related compounds are therefore of great interest as therapeutic agents, being useful for the treatment and prophylaxis of various human and animal diseases related to calcium imbalance. As a result, there has been much effort directed towards the synthesis of such 1-hydroxyvitamin D compounds, and a variety of useful procedures are documented in the patent and other literature.

Of relevance to the present application is the synthetic method described by Paaren et al. in J. Org. Chem. 45, 3253 (1980) and DeLuca et al. in U.S. Pat. Nos. 4,195,027 and 4,260,549 which disclosures relate to the preparation of 1α-hydroxyvitamin D derivatives from vitamin D compounds by hydroxylation at carbon 1. Briefly, this method involves the tosylation of a vitamin D compound at the C-3-hydroxy group, followed by tosyl displacement with formation of a 3,5-cyclovitamin D derivative, and subsequent oxidation of that intermediate to a 1α-hydroxy-3,5-cyclovitamin D which is then converted to the C-1-acyloxy derivative and subsequently solvolyzed under acid catalysis to obtain a mixture of the 5,6-cis- and 5,6-trans-1α-hydroxyvitamin D 1-O-acylates. Alternatively, the free 1α-hydroxy-3,5-cyclovitamin D intermediate can be directly solvolyzed in an acid medium (e.g. a low-molecular-weight organic acid, such as formic or acetic acid) to obtain a mixture of the 5,6-cis- and 5,6-trans-1α-hydroxy-vitamin D 3-O-acylates, where the acyl group originates, in this case, from the said medium used.

It will be noted, that the methods taught by the prior art produce the 1- or 3-O-acyl derivatives of the 1α-hydroxyvitamin D compounds, and since the free (unprotected) 1α-hydroxyvitamins are generally the desired products, these acyl groups must be removed by a subsequent hydrolysis or reduction step.

DISCLOSURE OF INVENTION

A new process has now been developed which yields directly the desired free 1-hydroxyvitamin D compounds thus eliminating the need for the additional acyl-removal step of the known process described above. This process comprises the acid-catalyzed solvolysis of a 1-hydroxy-3,5-cyclovitamin D compound to obtain directly a mixture of 1-hydroxyvitamin D (5,6-cis compound) and 5,6-trans-1-hydroxyvitamin D, i.e. the free, non-acylated, hydroxyvitamin D compounds.

More specifically, the 1-hydroxy-3,5-cyclovitamin D compound is dissolved in a mixture of dimethylsulfoxide and a low-molecular weight organic acid, e.g. glacial acetic acid, halo-substituted acetic acids or formic acid. An equimolar ratio of dimethylsulfoxide and acid, or a slight excess of acid is preferred. This reaction mixture is then warmed to a temperature ranging from ca. 30° to ca. 100° C., in an inert atmosphere for a time sufficient to achieve complete reaction. In general, reaction temperatures of about 50° C. and reaction times of 0.5 to 1 hr are appropriate. Under such conditions, the 1-hydroxy-cyclovitamin derivative is solvolyzed to yield the free hydroxyvitamin D product, namely the mixture of 1-hydroxyvitamin D and its 5,6-trans-isomer, in a ratio of about 4 to 1.

Preferred 3,5-cyclovitamin D compounds to be used in the above described process are the 1α-hydroxy-3,5-cyclo-vitamin D compounds, characterized by the general structure shown below

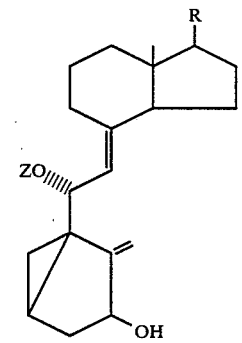

wherein Z is an alkyl group, and R is a steroid side chain of the type

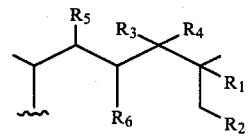

wherein each of $R_1$, $R_2$ and $R_3$ is selected from the group consisting of hydrogen, hydroxy, protected hydroxy, and halogen, and where $R_4$ is hydrogen, halogen or alkyl, and $R_5$ and $R_6$ represent, independently, hydrogen, hydroxy, protected hydroxy and halogen, or taken together, form a carbon-carbon bond. Particularly preferred are cyclovitamin compounds in which the side chain R has the structure of the side chain of vitamin $D_3$ or of vitamin $D_2$. Also preferred are the compounds in which R is a side chain as it occurs in 25-hydroxyvitamin $D_3$, 25-hydroxyvitamin $D_2$, 25-hydroxy-24-epivitamin $D_2$, 24,25-dihydroxy-vitamin $D_3$ and 25,26-dihydroxyvitamin $D_3$.

Wherever used in this specification and the claims, the term "alkyl" denotes a hydrocarbon radical of 1 to 6 carbons, in all isomeric forms, e.g. methyl, ethyl, propyl, isopropyl, butyl, isobutyl, t-butyl, pentyl, hexyl, etc., the term "protected hydroxy" denotes a hydroxy function protected by acyl, alkylsilyl or ether groups. Acyl groups suitable for such function are, for example, alkanoyl groups of 1 to 6 carbons, e.g. formyl, acetyl, butyryl, hexanoyl, or aroyl groups such as benzoyl, or methyl-, halo- or nitro-substituted benzoyl, while examples of suitable ether protecting groups are methoxymethyl, ethoxymethyl, tetrahydrofuranyl or tetrahydropyranyl.

The 1α-hydroxy-3,5-cyclovitamin D can be prepared by the general procedures given in U.S. Pat. No. 4,195,027. This preparative procedure involves the 1-hydroxylation of the corresponding 3,5-cyclovitamin D compound by treatment of the latter with $SeO_2$ and a hydroperoxide (typically t-butyl hydroperoxide) in an organic solvent such as chloroform or methylene chloride. It has been found that the yield of the desired 1α-hydroxy-3,5-cyclo-vitamin D product is increased (and the amount of undesired side products, e.g. the 1-oxo-compounds is substantially decreased) when the reaction is conducted with substantially anhydrous hydroperoxide (e.g. anhydrous t-butylhydroperoxide in toluene, prepared according to the method of Sharpless et al., J. Org. Chem. 48, 3607 (1983)) and in the presence of a small amount of a nitrogenous base, e.g. pyridine. For example, a reaction mixture containing 0.5 equivalent of $SeO_2$, 2 equivalents of t-butylhydroperoxide (as a ca. 3M solution in toluene), 1 equivalent of pyridine and 1 equivalent of the 3,5-cyclovitamin D compound to be oxidized, all dissolved in an organic solvent such as methylene chloride, gives a substantially improved yield of the desired 1α-hydroxy-3,5-cyclovitamin D compound.

Solvolysis of such 1α-hydroxy-3,5-cyclovitamins in dimethylsulfoxide/organic acid as specified above leads to a product mixture comprising 1α-hydroxyvitamin D and 1α-hydroxy-5,6-trans-vitamin D, characterized, respectively, by the structures shown below wherein R is a side chain as defined above.

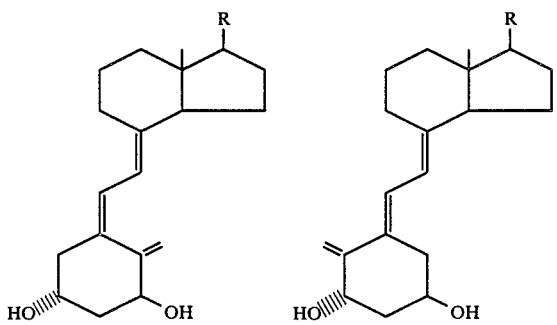

Such product mixture, which consists predominantly of the 5,6-cis product can be used as such for therapeutic purposes, or it may be separated, e.g. by chromatographic methods, such as high performance liquid chromatography, to obtain either of the compounds in pure form. However, as mentioned above, direct chromatographic separation of such mixtures is exceedingly tedious and difficult especially on a preparative scale. A preferred method for the separation of such mixtures consists of treatment of the mixture as obtained by the above-described solvolysis method, with a dienophile in an organic solvent, so as to obtain a mixture comprising the dienophile adduct of the 5,6-trans compound and the unreacted 5,6-cis vitamin compound. The adduct and the free 5,6-cis compound are then easily separated by standard chromatography so as to obtain the 1-hydroxy-vitamin D product in pure form. Examples of suitable dienophiles are acrylic acid and alkyl esters thereof, acetylenic acids and esters, acetylene dicarboxylic acid and mono- or di-alkyl esters thereof, maleic acid and its derivatives, such as maleic anhydride, maleimide, N-substituted maleimides, and maleic acid esters, as well as nitrogen-dienophiles such as N4-alkyl or N4-phenyl-substituted triazoline-3,5-dione, or the alkyl esters of azo-dicarboxylic acid.

When a mixture of 5,6-cis- and 5,6-trans-1α-hydroxyvitamin D compounds is treated with such a dienophile, the trans compound in the mixture reacts preferentially to form the Diels-Alder adduct between the dienophile and the 5,6-trans-compound. This adduct is conveniently separated from the unreacted 5,6-cis compound by chromatography, so as to recover the latter in pure form. Alternatively, whenever the dienophile contains an acid, or hydrolyzable ester, or anhydride group, the mixture of adduct and free 5,6-cis compound, may be treated with a base, which converts the acid to the carboxylate and saponifies the anhydride or ester groups to carboxylate groups, thus rendering the dienophile-adduct of the 5,6-trans-vitamin D compound water soluble, so that the trans-product can be removed by simple partitioning between an aqueous and organic solvent with the desired 5,6-cis-1-hydroxyvitamin D compound being recovered in the organic phase.

The reaction of cis/trans-1-hydroxyvitamin D mixtures with dienophile can be conducted in a wide range of organic solvents (e.g. aliphatic or aromatic hydrocarbon solvents, halo-carbon solvents, ethers, or low-molecular weight ester solvents), the temperature and time of reaction being adjusted so as to give complete reaction with the 5,6-trans-compound. To assure complete reaction, the dienophile is preferably added in some excess over the amount of 5,6-trans-compound estimated to be present in the mixture (e.g. 1.5-5-fold molar excess). Reaction temperatures of from below 0° C. to the boiling temperature of the solvent are appropriate, the temperature and time being selected in accordance with the inherent reactivity of the dienophile chosen, as is well-understood in the art. For example, for the reaction of a cis/trans-1α-hydroxyvitamin D mixture with maleic anhydride a reaction temperature of 30°-40° C. and reaction time of from 12-24 hr is suitable. At higher temperatures, e.g. 50°-60° C., a reaction time of 1-2 hr is adequate, at about 80° C., reaction time is reduced to about 10-30 min.

The above described solvolysis procedure can also be applied to 1β-hydroxy-3,5-cyclovitamin D compounds, i.e. compound of the general structure

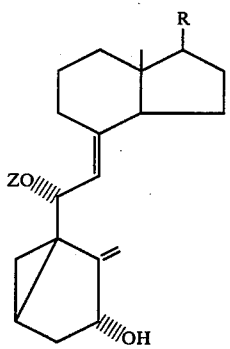

wherein Z and R represent substituents as defined above. Solvolysis of these 1β-hydroxy-epimers in dimethylsulfoxide/organic acid under the conditions specified above leads to a mixture of 1β-hydroxyvitamin D and 1β-hydroxy-5,6-trans-vitamin D which may be separated, if desired, by the procedures previously described. Furthermore, mixtures of 1α-hydroxy- and 1β-hydroxy-3,5-cyclovitamin D compounds can be solvolyzed whereby a product mixture comprising 1α-hydroxyvitamin D and the corresponding 5,6-trans-isomer, and 1β-hydroxyvitamin D and its 5,6-trans-isomer is obtained. If individual compounds are desired, the 1α-hydroxy-epimers can be separated from the 1β-hydroxy compounds by direct chromatography (e.g. high pressure liquid chromatography) or via boronate ester formation and chromatography (as described in U.S. Pat. No. 4,338,250) and the 5,6-cis/trans pairs can then be separated by additional chromatography on high performance columns or by the dienophile-adduct method as described above.

The 1β-hydroxy-3,5-cyclovitamin D compounds are obtained as minor products in the 1-hydroxylation process using selenium dioxide and t-butylhydroperoxide as described above, or may be obtained by hydride reduction, under standard conditions, of the known 1-oxo-3,5-cyclovitamin D compounds.

EXAMPLE 1

Solvolysis of 1α-hydroxy-3,5-cyclovitamin $D_3$

A solution of 1α-hydroxy-3,5-cyclovitamin $D_3$ (1 g) in a mixture of dimethylsulfoxide (10.64 ml, 0.15 mole) and glacial acetic acid (8.59 ml, 0.15 mole) was heated to 50° C. under $N_2$ for 1 hr. The mixture was then poured over ice, and extracted with ether (3×75 ml). (Alternatively, the mixture can be neutralized by addition of $NaHCO_3$ solution, prior to ether extraction.) The combined extracts were washed with saturated aqueous $NaHCO_3$, water, and saturated NaCl solution, then dried over $MgSO_4$, filtered and concentrated in vacuo to give a mixture containing in ca. 4:1 ratio 1α-hydroxyvitamin $D_3$ (5,6-cis-compound) and 5,6-trans-1α-hydroxyvitamin $D_3$.

EXAMPLE 2

Separation of 5,6-cis and trans-1α-hydroxyvitamin D compounds by reaction with a dienophile A mixture of 5,6-cis- and 5,6-trans-1α-hydroxyvitamin $D_3$ compounds, as obtained in Example 1 above, was dissolved in ethyl acetate (25 ml) and treated with freshly recrystallized maleic anhydride (4-fold molar excess of the estimated amount of 5,6-trans-compound present). This reaction mixture was heated to 35° C. under $N_2$ for 24 hr. After evaporation of the solvent in vacuo, the crude oil was chromatographed over a silica gel column (2×30 cm) using ethyl acetate/hexane mixtures as eluent. The fractions containing the desired 1α-hydroxyvitamin $D_3$ were collected and pooled, and this material was repeatedly crystallized from methyl-formate to give the pure product (mp 135°–137° C.).

EXAMPLE 3

Separation of a mixture of 5,6-cis and trans 1α-hydroxyvitamin $D_3$ by dienophile-reaction and saponification A mixture of 5,6-cis- and 5,6-trans-1α-hydroxyvitamin $D_3$, dissolved in ethyl acetate was reacted with maleic anhydride as in Example 2 above. After completion of reaction (24 hr, at 35° C.), the solvent was removed in vacuo and the resulting residue was treated with an aqueous solution of sodium hydroxide (25 ml) for 10–20 min at room temperature (to saponify the maleic anhydride adduct of the 5,6-trans-compound). Ether was then added and the phases were separated in a separating funnel. After further ether extraction of the aqueous phase, the pooled ether phases were washed with 10% aqueous NaOH, water, and saturated NaCl solution, and then dried over $MgSO_4$. Evaporation of the ether solvent gave crude 1α-hydroxyvitamin $D_3$ product, which was further purified by chromatography over silica gel (ethyl acetate/hexane mixtures as eluent) and then crystallized from methyl-formate to obtain the desired 1α-hydroxyvitamin $D_3$.

EXAMPLE 4

Improved 1α-hydroxylation of 3,5-cyclovitamin $D_3$

Anhydrous tert-butyl hydroperoxide (26 mmole) in toluene (9.0 ml) was added to a stirred suspension of selenium dioxide (0.722 g, 6.5 mmole) in dry methylene chloride (150 ml) in a three-necked flask. The mixture was stirred for 3 hr under a slight positive pressure of nitrogen. Pyridine (1.05 ml, 13 mmole) was then added, and then 3,5-cyclovitamin $D_3$ (13 mmole) was introduced as a solution in methylene chloride (50 ml). After 30 min, 10% aqueous NaOH solution (70 ml) was added, and then the reaction mixture was diluted with ether (500 ml) and the phases were separated. The organic phase was washed with 10% NaOH (3×70 ml), then with water and saturated NaCl solution, and dried over $MgSO_4$. After filtration and evaporation of the solvent, the crude 1α-hydroxy-3,5-cyclovitamin $D_3$ product was purified by chromatography over Florisil (6×35 cm column). Elution with ethyl acetate/hexane mixtures, and pooling of appropriate fractions gave 3.65 g of the desired 1α-hydroxy-3,5-cyclovitamin $D_3$ product (ca. 85–90% pure).

We claim:

1. A method for preparing 1-hydroxyvitamin D compounds, which comprises treating a 1-hydroxy-3,5-cyclovitamin D compound with a mixture of dimethylsulfoxide and an organic acid, whereby the non-acylated 1-hydroxyvitamin D compound and its 5,6-trans-isomer are obtained in admixture and, optionally, separating said mixture to recover one or both 1-hydroxyvitamin D components.

2. The process of claim 1 wherein the organic acid is acetic acid or formic acid.

3. The process of claim 1 wherein the 1-hydroxy-3,5-cyclovitamin D compound is 1α-hydroxy-3,5-cyclovitamin $D_3$.

4. The process of claim 1 wherein the 1-hydroxy-3,5-cyclovitamin D compound is 1α-hydroxy-3,5-cyclovitamin $D_2$.

5. The process of claim 1 wherein the 1-hydroxy-3,5-cyclovitamin D compound is 1α,25-dihydroxy-3,5-cyclovitamin $D_3$.

6. The process of claim 1 wherein the 1-hydroxy-3,5-cyclovitamin D compound is 1α,25-dihydroxy-3,5-cyclovitamin $D_2$ or 1α,25-dihydroxy-3,5-cyclo-24-epivitamin $D_2$.

7. The process of claim 1 wherein the separation of the mixture of 5,6-cis- and 5,6-trans-1-hydroxyvitamin D isomers is accomplished by treating said mixture with a dienophile.

8. The process of claim 7 wherein the dienophile is selected from the group consisting of maleic acid, maleic acid monoalkyl ester, maleic acid dialkyl ester, maleic anhydride, acetylene dicarboxylic acid, and acetylene alkyl dicarboxylate.

9. The method of claim 7 wherein the dienophile is selected from the group consisting of N4-alkyl or phenyl-substituted-triazoline-3,5-dione, maleimide, and N-alkyl or phenyl-substituted maleimide.

10. The process of claims 7 or 9 wherein the product mixture resulting from treatment with a dienophile is separated by chromatography.

11. The process of claims 7 or 8 wherein the product mixture resulting from treatment with a dienophile is separated by treatment with a base and partitioning between an aqueous and organic solvent, and recovering the desired 1-hydroxyvitamin D product in the organic solvent.

* * * * *